United States Patent
Hare et al.

(10) Patent No.: US 6,209,589 B1
(45) Date of Patent: Apr. 3, 2001

(54) APPARATUS AND METHOD FOR DISTRIBUTING BEADS

(75) Inventors: John Francis Hare, London; Philip John James, Welwyn Garden City; Richard C. Payne, Harpenden; John Barry Marlow, Hoddesdon, all of (GB)

(73) Assignee: SmithKline Beecham plc, Brentford (GB)

(*) Notice: Subject to any disclaimer, the term of this patent is extended or adjusted under 35 U.S.C. 154(b) by 0 days.

(21) Appl. No.: 09/284,789

(22) PCT Filed: Oct. 17, 1997

(86) PCT No.: PCT/GB97/02883

§ 371 Date: Jun. 14, 1999

§ 102(e) Date: Jun. 14, 1999

(87) PCT Pub. No.: WO98/17383

PCT Pub. Date: Apr. 30, 1998

Related U.S. Application Data

(63) Continuation of application No. 08/734,228, filed on Oct. 21, 1996, now abandoned.

(51) Int. Cl.[7] .................. B65B 1/04; B65B 3/04
(52) U.S. Cl. .................. 141/1; 141/9; 141/94; 141/100; 141/129; 141/130; 141/279; 222/71; 250/222.2; 377/10
(58) Field of Search .................. 141/1, 9, 31, 67, 141/94, 129, 130, 135, 153, 183, 192, 270, 279, 100; 222/40, 52, 71; 377/10; 250/222.2

(56) References Cited

U.S. PATENT DOCUMENTS

| | | | |
|---|---|---|---|
| 2,656,508 | 10/1953 | Coulter | 324/71 |
| 3,710,933 | 1/1973 | Fulwyler et al. | 209/3 |
| 4,170,699 | 10/1979 | Wright | 526/215 |
| 4,818,492 | 4/1989 | Shimizu | 73/863 |
| 5,076,097 | 12/1991 | Zarrin et al. | 73/61 |
| 5,245,530 | 9/1993 | Taki | 73/863 |
| 5,290,707 | 3/1994 | Wood | 436/523 |
| 5,415,051 | 5/1995 | Rokugawa et al. | 73/863 |
| 5,649,576 | 7/1997 | Kirk et al. | 141/129 |

FOREIGN PATENT DOCUMENTS

WO 91/17823  11/1991  (WO) .............. C07K/1/04

Primary Examiner—Timothy L. Maust
(74) Attorney, Agent, or Firm—S. Venetianer

(57) ABSTRACT

Substrate beads for combinatorial synthesis are selected individually from a mixture by suspending the mixture in an electrically conductive liquid, in a bead selection vessel, causing the liquid to flow at a controlled rate through an aperture in the side wall of a pipette extending through the vessel, and detecting the passage of a bead through the aperture by monitoring an electrical resistance across the aperture. In an alternative embodiment, beads are passed through a tube into a collection passage in which a continuous laminar flow takes place. Detection takes place at the tip of the tube, and, in response to the detection of a bead, the flow through the collection passage is diverted to cause the bead to be deposited. In both cases, the selected bead is deposited into a well of a plate having rows and columns of wells in a rectangular array, while a vacuum is drawn through a filter in the bottom of the well. The bead selection head is moved from well to well in each column, and the well plate is indexed to position the columns successively underneath the path of the bead selection vessel. A plate handling mechanism retrieves plates from a supply stack, moves them laterally underneath the bead selection vessel, and elevates them into another stack.

6 Claims, 7 Drawing Sheets

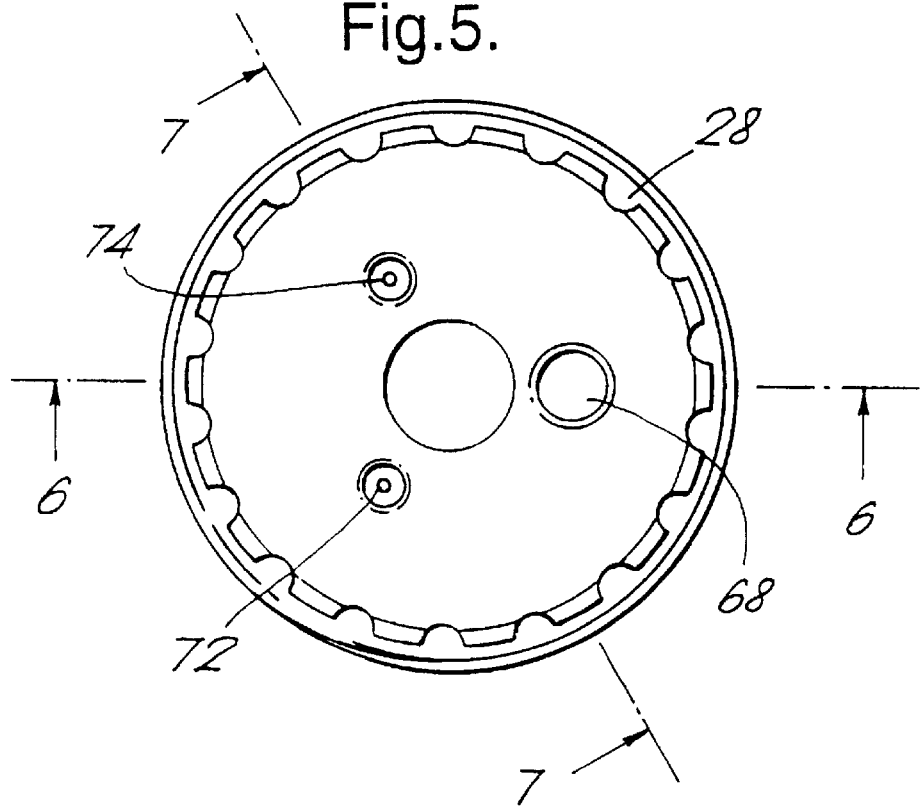
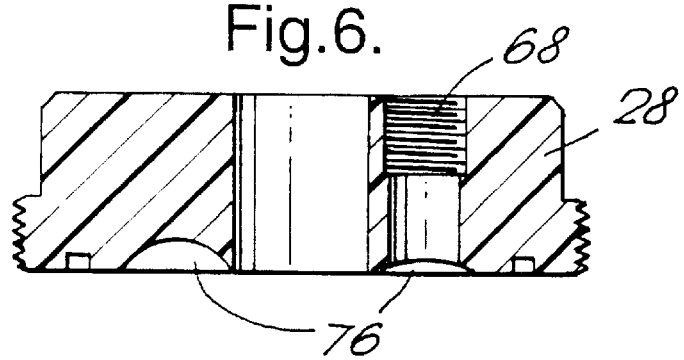
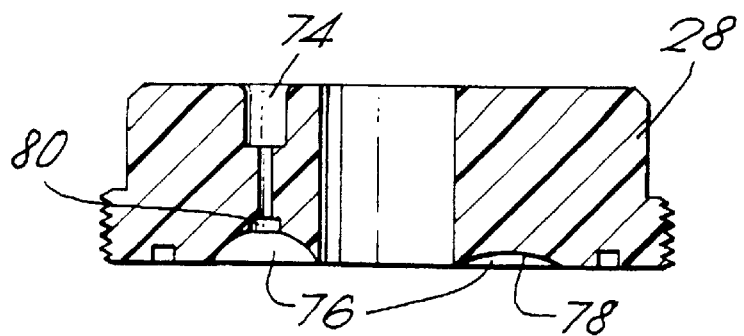

APPARATUS AND METHOD FOR DISTRIBUTING BEADS

This application is a 371 of PCT/GB97/02883 filed Oct. 17, 1997 which is a continuation of Ser. No. 08/734,228 filed Oct. 21, 1996 Abandon.

FIELD OF THE INVENTION

This invention relates to chemical synthesis, and more particularly to an improved apparatus and method for distributing microscopic beads of the kind used as substrates in combinatorial chemistry.

BACKGROUND OF THE INVENTION

In combinatorial synthesis, it is often desirable to be able to distribute beads into a two-dimensional array, so that each variant in a combinatorial library can be identified by its position in the array. The array can consist of a set of plates, each having rows and columns of wells, with one bead, or some other predetermined number of beads, in each well. The beads are typically made of polystyrene, and serve as substrates for different compounds produced in the process of split and combine synthesis. Ultimately, the synthesized compounds are stripped from the beads and tested for activity. The identity of an active compound is determined by spectrographic analysis, in the light of the information available concerning the reaction histories of the beads being distributed.

The beads are spherical and of extremely small size, e.g. 300 mm in diameter. Consequently, they are difficult to handle, and it has been very difficult to separate a single bead from a mixture of beads.

SUMMARY OF THE INVENTION

The principle object of this invention is to provide an apparatus and method for selecting individual beads, or preselected numbers of beads from a mixture of beads, and distributing the selected beads into a two-dimensional array.

A further object of the invention is to provide a bead distribution apparatus which is both simple and highly reliable.

This apparatus utilizes a head similar to that of a "Coulter" counter, a device used to count and size particles in a liquid. For example, it is used in the petroleum industry to assess engine wear by counting particles in lubricating oil. The principle on which the Coulter counter operates is that electrical resistance of a conductive fluid, measured by electrodes on both sides of a small aperture, increases momentarily as a solid particle passes through the aperture. The passage of particles through the aperture is detected as a electrical pulses, which can be counted electronically. The Coulter counter is described in detail in U.S. Pat. No. 2,656,508, issued Oct. 20, 1953, and the disclosure of that patent is here incorporated by reference.

The preferred embodiment of this invention takes advantage of the principle of the Coulter counter, but uses the principle in a different way and for a different purpose.

In accordance with the invention, beads, from a mixture of beads, preferably of substantially uniform size, are distributed into an array having multiple locations, so that a predetermined number of beads is deposited at each location in the array. This is carried out by forming a suspension of the mixture of beads in a carrier liquid; causing a part of the liquid to flow through an aperture of a size such that the beads can pass through the aperture only one at a time; detecting the passage of a predetermined number of the beads through the aperture; and, in response to the detection of the passage of the predetermined number of the beads through the aperture, depositing them at a predetermined location of the array.

In one embodiment of the invention, the selection of beads to be deposited is carried out by discontinuing the flow through the aperture upon detection of the passage of the predetermined number of the beads through the aperture. In an alternative embodiment, flow takes place continuously through the aperture, and is diverted in response to a detection signal to effect bead deposition.

The carrier liquid is electrically conductive, and is stirred to keep the beads in suspension. In a first embodiment, to deposit a single bead, a syringe is operated to produce a steady flow of liquid through an aperture in the side wall of a tube extending through the container for the carrier liquid. Eventually, a bead will pass through the aperture along with the liquid. When the passage of a bead is detected electrically, the operation of the syringe is discontinued and the flow of liquid through the aperture stops. This prevents other beads from passing through the aperture. After its passage through the aperture is detected, the bead is flushed out of the tube by a pumped liquid, and deposited at its location in the array, preferably into a well in a well plate. Preferably, while the syringe is causing liquid to flow into the tube through the aperture, liquid is withdrawn from the upper end of the tube by a pump at the same rate at which it flows into the tube through the aperture. This prevents liquid from passing through the lower end of the tube. Normally only one bead will be deposited at each location in the array. However, multiple beads can be deposited at each location. This is done by counting the electrical pulses corresponding to peaks in resistance. When the desired number of beads is counted, the flow of the suspension liquid is discontinued.

In a second embodiment, the aperture at which detection takes place is at the end of a tube through which liquid flows continuously. When a bead is detected at the aperture, a signal is produced causing the flow of liquid to be diverted so that the bead is carried to the location at which it is to be deposited.

In a preferred embodiment of the invention, a stack of empty well plates is initially placed in the apparatus. The lowermost well plate in the stack is automatically moved to a position underneath the head with a first row of wells positioned underneath, and parallel to a linear path of movement of the head. The head moves successively from one well to the next, depositing a bead in each well of the column. The well plates are indexed laterally to position successive rows of wells underneath the path of the head. When a plate is filled, i.e. it has one bead in each of its wells, it is moved into a new stack and the apparatus retrieves a new plate from the supply stack and begins to distribute beads to the new plate.

Further objects, details and advantages of the invention will be apparent from the following detailed description, when read in conjunction with the drawings.

BRIEF DESCRIPTION OF THE DRAWINGS

FIG. 5 is a top plan view of the cover of the bead distribution head;

FIG. 6 is a section taken on plane 5—5 in FIG. 4; and

FIG. 7 is a section taken on plane 6—6 in FIG. 4;

DETAILED DESCRIPTION

Figure 1:
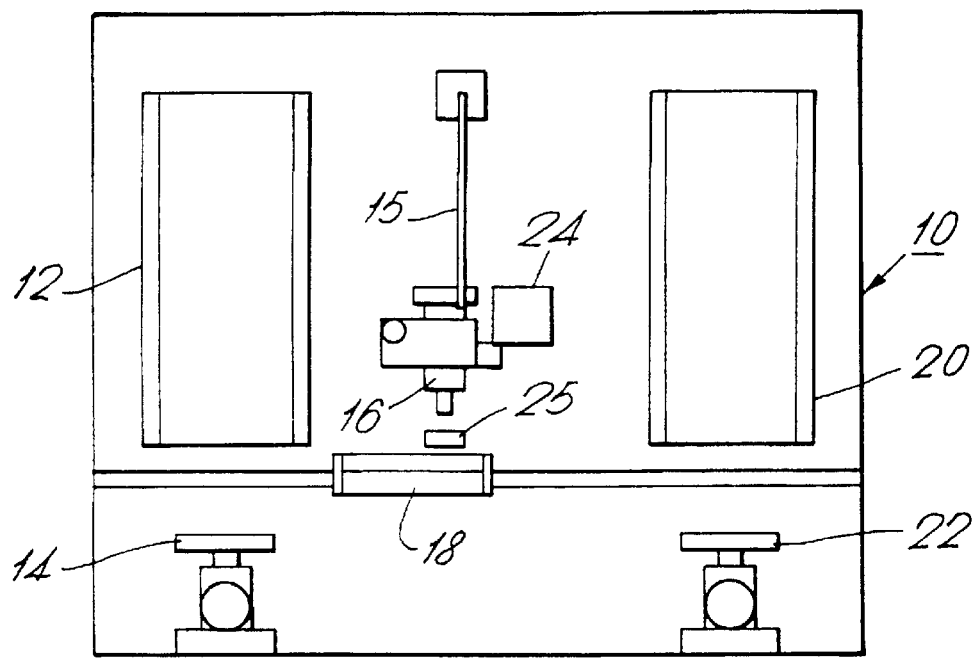
FIG. 1 is a diagrammatic front view of a bead distribution apparatus, showing a movable bead distribution head, and mechanisms for transporting well plates from a supply stack to a location underneath the distribution head, and from the distribution head to a second stack.
Figure 2:
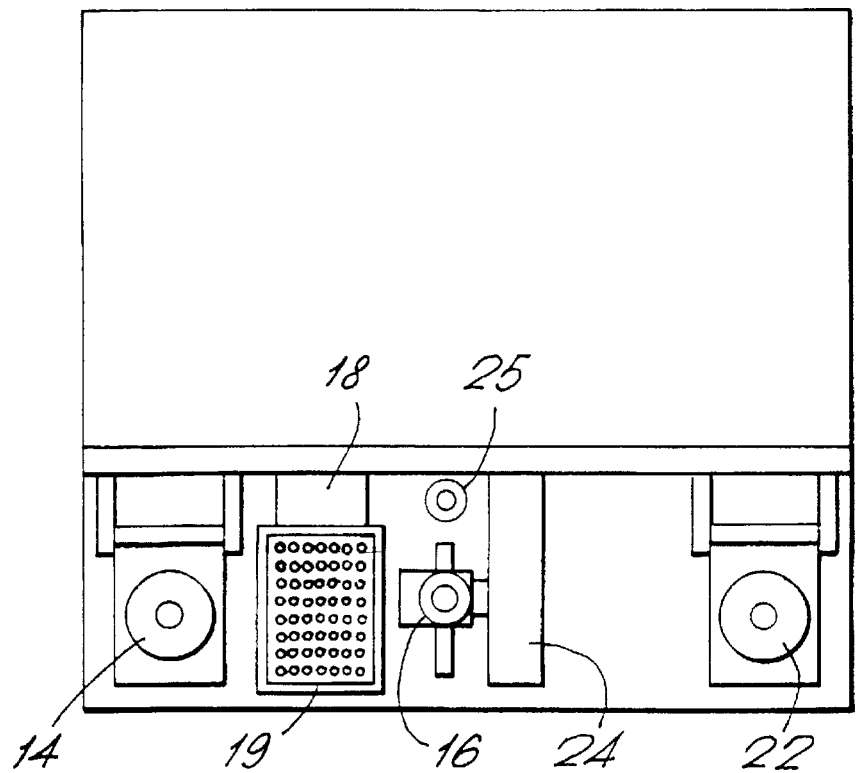
FIG. 2 is a diagrammatic top plan view of the bead distribution apparatus.

Referring to FIGS. 1 and 2, the bead distribution apparatus 10 comprises a loading guide 12 in which empty well plates, of a standard, commercially available type, may be stacked. The empty well plates are unloaded from the bottom of guide 12 by an unloader 14 into a conveyor 18, and are transferred individually by the conveyor to a position underneath a distribution head 16. Each well plate, e.g. well plate 19 in FIG. 2, has a rectangular array of wells disposed in rows and columns. While a well plate is underneath the distribution head, the distribution head moves from well to well in a row (perpendicular to the plane of FIG. 1), depositing a bead in each well. When the distribution head has traversed a row of wells, the conveyor 18 indexes the well plate to position a next row underneath the path of the head. This is repeated until beads are deposited in all of the wells. Then the conveyor moves the well plate to a position underneath a stacking guide 20, and the well plate is loaded into the stacking guide by a stacker 22.

The unloader 14 and the stacker 22 are elevators with platforms which engage the lowermost well plates in the guides and move vertically to load and unload the conveyor. Catches (not shown in FIGS. 1 and 2) are provided at the lower end of the loading guide 12 for supporting the stack of well plates in the loading guide when the unloader 14 is retracted. These catches are electrically operated, and microprocessor controlled so that they cooperate with the unloader 14, allowing the unloader to receive a well plate from the loading guide 12 and deposit the well plate onto the conveyor. Ratchet-type catches (not shown in FIGS. 1 and 2) are provided at the lower end of the stacking guide 20 to support well plates in the stacking guide while allowing the stacker 22 to deposit the well plates therein.

While the well plate is underneath the distribution head 16, a bead is deposited in each well, the distribution head being indexed from well to well in each row of wells along a supporting arm 24. The distribution head can also be moved to a position just above a waste collector 25, which, as shown in FIG. 2, is located behind the path of movement of the well plates.

The distribution head supporting arm 24 is itself movable vertically so that the distribution head can be moved up and down. All of the fluid conducting lines and electrical leads to the distribution head 16 are flexible, and preferably bundled together in a single flexible sheath 15 (FIG. 1), so the that the distribution head can move freely.

Figure 3:
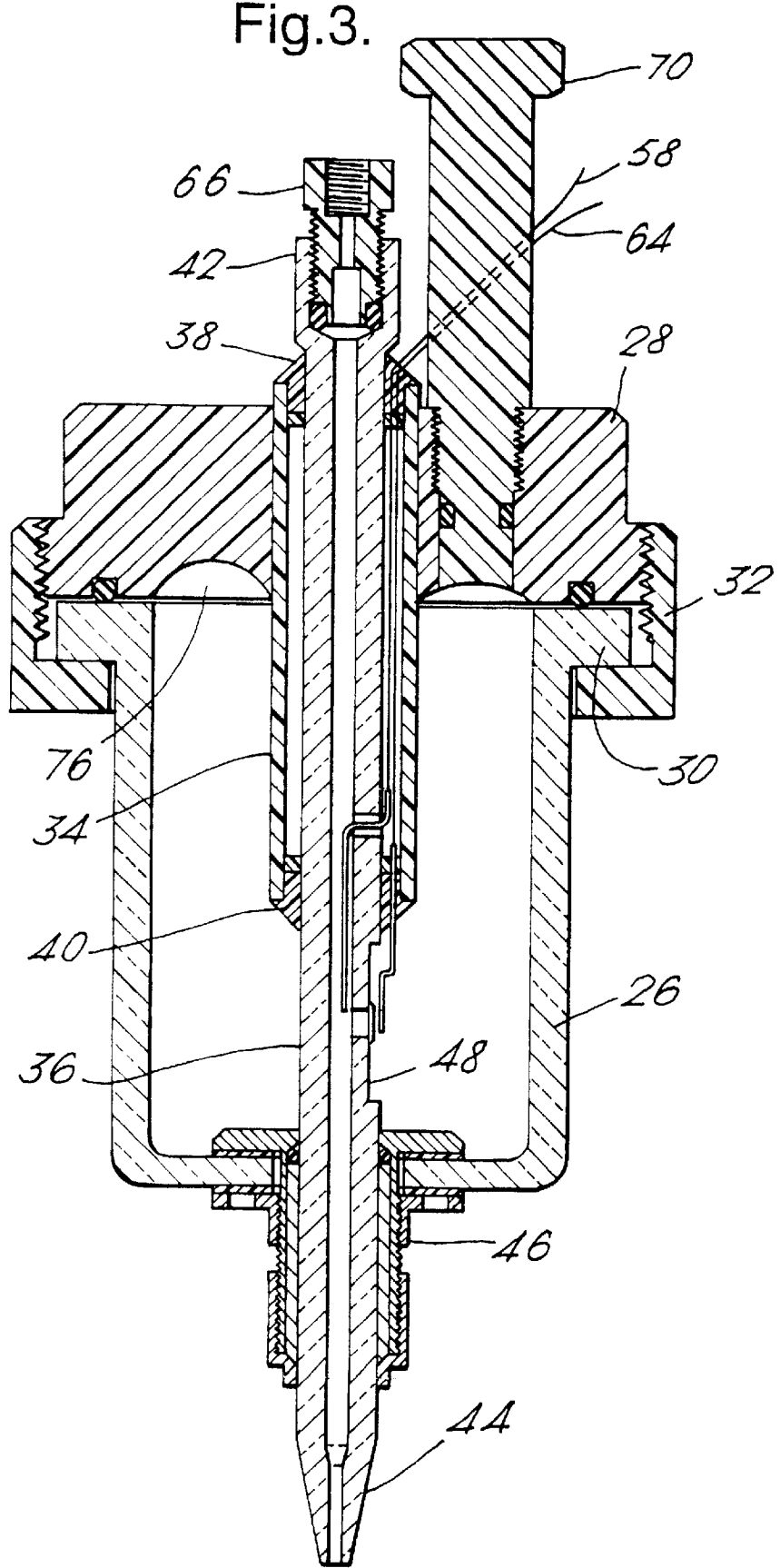
FIG. 3 is a vertical section through the bead distribution head.

The distribution head, shown in detail in FIG. 3, comprises a cup-shaped vessel 26 having a cover 28 secured to a flange 30 of the vessel by a threaded ring 32. A sleeve 34 extends through the center of the cover, and a pipette 36 is held in the sleeve by seals 38 and 40. The pipette extends through vessel 26, its upper end 42 being located above the cover 28, and its lower end 44 being below the bottom of the vessel. The pipette extends through a seal 46 at the bottom of the vessel.

Figure 4:
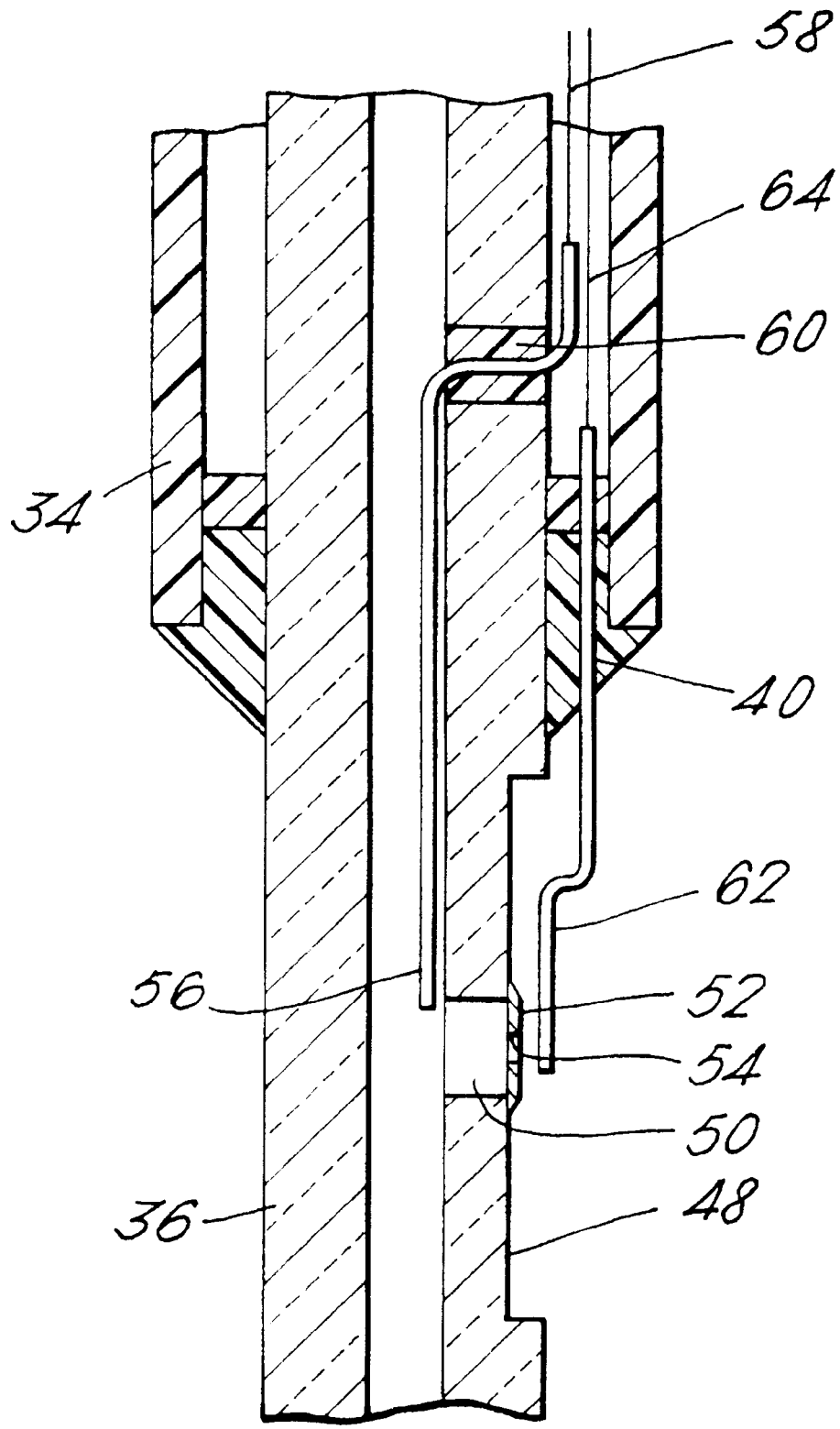
FIG. 4 is a fragmentary sectional view, showing details of the bead selection aperture in the bead distribution head.

The outside wall of the pipette is cylindrical throughout most of its length. However, a flat area 48 is formed on the outer wall of the pipette at a location within the interior of the vessel 26 just below the lower end of sleeve 34. As shown in FIG. 4, an opening 50 is formed in the wall of the pipette within the flat area 48, and a small watch jewel 52, having an accurately machined aperture 54 is secured to the flat area by an adhesive, with aperture 54 in register with opening 50. The aperture 54 is typically 500 mm in diameter, but can be larger or smaller, depending on the size of the beads to be distributed. In general, the diameter of the aperture should be less than twice the diameter of the beads. Alternatively, the aperture can be formed directly in the wall of the pipette, obviating the use of the jewel.

As shown in FIG. 4, a first platinum electrode 56 is located within the pipette, with its tip adjacent to opening 50. Electrode 56 extends through a seal 60 in the wall of the pipette and is connected to a flexible, multistrand lead 58, which is isolated from the suspension in vessel 26 by sleeve 34. Another platinum electrode 62 has its tip located adjacent to the outer end of aperture 54, and extends through seal 40 into the space between the pipette and the inner wall of sleeve 34, where it is connected to a flexible lead 64.

Returning to FIG. 3, the top of the pipette is provided with a fitting 66 for connection to a pump. The pump (not shown in FIG. 3) is used to withdraw liquid from the upper end of the pipette as it flows into the pipette through aperture 54. The pump is also used to deliver liquid for flushing selected beads out through the lower end of the pipette.

FIGS. 5, 6 and 7 show that the cover 28 has three additional openings besides its central opening through which sleeve 34 extends. The first opening, 68, is an opening for introducing beads into the vessel, and is closable by a removable threaded plug 70 (FIG. 3). The second opening, 72, is an inlet for connection to a syringe used to produce flow of liquid into vessel 26. The third opening, 74, is a vent opening. As shown in FIGS. 3, 6 and 7, the underside of the cover 28 has an annular groove 76 which varies in depth, with its deepest point being at the location of vent opening 74. The groove becomes continuously shallower in both directions from the vent opening toward a shallowest point 78 (FIG. 7) opposite the vent opening so that air can be exhausted completely from the vessel. A porous filter 80 is provided in the vent opening.

Figure 8:
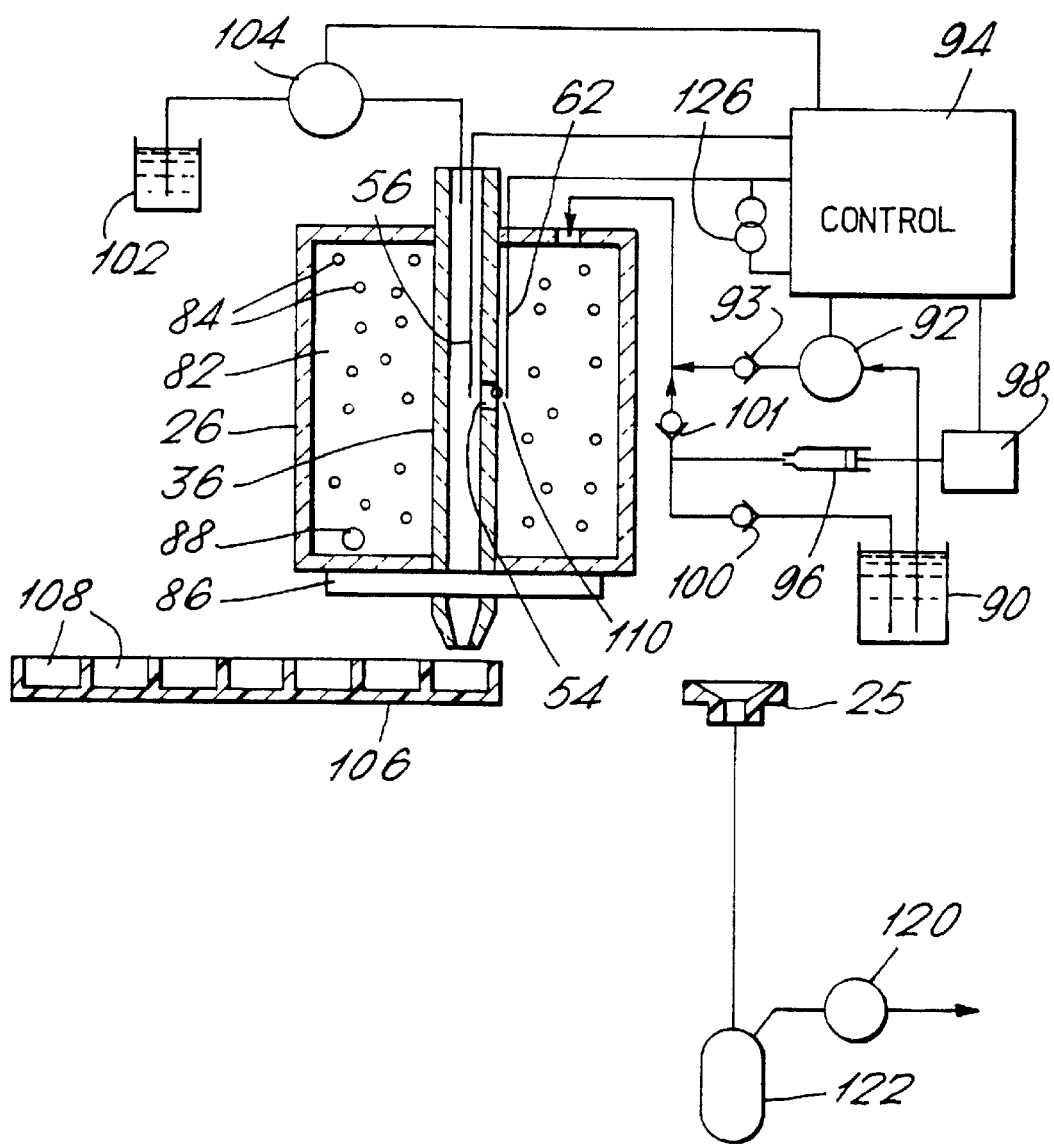
FIG. 8 is a schematic diagram showing the fluid paths and controls of the apparatus, and illustrating the manner in which a bead is selected from a suspension of beads in a liquid.

FIG. 8 shows vessel 26 filled with a suspension consisting of a liquid 82 and beads 84, held in suspension by an external magnetic stirring mechanism 86 cooperation with an agitator 88 inside the vessel. The density of the beads 84 is preferably greater than that of the liquid, so that they sink in the liquid. To prevent surface tension from causing the beads to float, they are pre-treated so that they are wetted by the liquid.

An example of an ideal liquid for use with polystyrene beads is a solution of ammonium acetate (2% w/w), and ammonium carbonate (2% w/w).

The liquid 82 is supplied to vessel 26 from a supply container 90 through a peristaltic pump 92, which is controlled by a control unit 94, and a check valve 93. A syringe 96 is used to control the flow of the liquid after the vessel 26 is filled. The syringe is operated by an actuator 98, controlled by the control unit. When the plunger of the syringe is withdrawn, the syringe draws liquid from supply container 90 through a check valve 100. Forward movement of the plunger causes the liquid to flow through check valve 101 into vessel 26.

A reversible peristaltic pump 104 is provided to withdraw liquid from the upper end of the pipette 36 as it flows into the pipette through aperture 54, and to pump liquid through the pipette from container 102 for the purpose of flushing beads out of the pipette either to the wells, or to the waste collector 25. Pump 104 is also under the control of unit 94.

In the operation of the system, the beads are introduced into the vessel 26 through opening 6 8 (FIGS. 5 and 6), which is then closed by plug 70 (FIG. 3). The control unit then operates pump 92 to fill the vessel with liquid from supply container 90. The operation of the pump 92 is discontinued when the vessel is filled with liquid. In the meanwhile, a well plate 106 is removed from the supply stack in guide 12 (FIG. 1) and moved into position underneath the vessel 26, which is a part of the distribution head.

The well plate 106, as shown in FIG. 1, comprises a two-dimensional rectangular array of wells 108 (FIG. 8), each of which is preferably closed at its bottom.

With the distribution head positioned so that the pipette is over the waste collector 25, the syringe 96 is operated to initiate a controlled flow of liquid at a constant rate into vessel 26 through check valve 101. While other kinds of pumps can be used to carry out this operation, the syringe is desirable because it is capable of producing a steady flow of liquid at a very slow rate. While the syringe 96 is causing liquid to flow into the vessel 26 and through the aperture 54 into the pipette 36, pump 104 is operated to withdraw liquid from the upper end of the pipette 36. The pump withdraws liquid at the same rate at which it is being introduced into the pipette by the operation of the syringe 96. The result is that liquid is prevented from being forced out the tip of the pipette, no matter how long it takes for a bead to pass through the aperture. This prevents unnecessary flow of liquid into the waste collector, and also prevents loss of beads through the tip of the pipette when multiple beads are being collected in the pipette for deposit into a well.

As seen in FIG. 8, a bead 110 in the suspension will eventually pass through aperture 54 into the interior of the pipette. The passage of the bead is detected by the control unit 94 as a change in the resistance measured between platinum electrodes 56 and 62. When the control unit detects the passage of a single bead, it causes actuator 98 to stop pushing the plunger of syringe 96 and simultaneously stops pump 104. As a result, the liquid flow through the aperture is discontinued, and only a single bead passes into the pipette. The control unit moves the distribution head to the next well in sequence, and after a predetermined delay, during which the bead inside the pipette settles by gravity to the tip of the pipette, the control unit activates pump 104 in the opposite direction for a short interval just sufficient to wash the bead out of the pipette 36 into the well.

The control unit then causes the distribution head to return to the waste collection point, and the bead depositing operation is repeated for each well in the row. After beads are deposited in each well in a row, the well plate is indexed to position another row of wells underneath the path of the distribution head. The bead depositing operation continues until beads are deposited in each well in the well plate, whereupon, the well plate is transferred to a position underneath the stacking guide 20, and elevated into the stacking guide. The movement of the well plates is depicted in FIG. 9.

Figure 9:
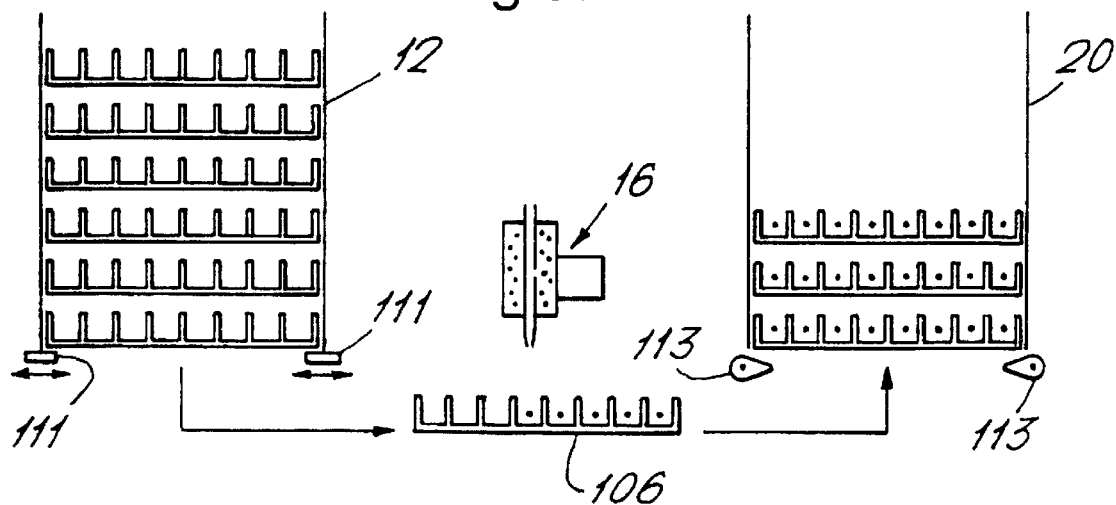
FIG. 9 is a schematic diagram illustrating the movement of well plates from the supply stack to a location underneath the distribution head, and from the distribution head to the second stack.

FIG. 9 also depicts laterally-slidable catches 111, which are operated by actuators (not shown) under the control of the control unit, for supporting the stack of well plates in the loading guide. Also shown are the ratchet-type catches 113, which support well plates in the stacking guide while allowing well plates to be raised into the stacking guide 20 by stacker 22.

Figure 10:
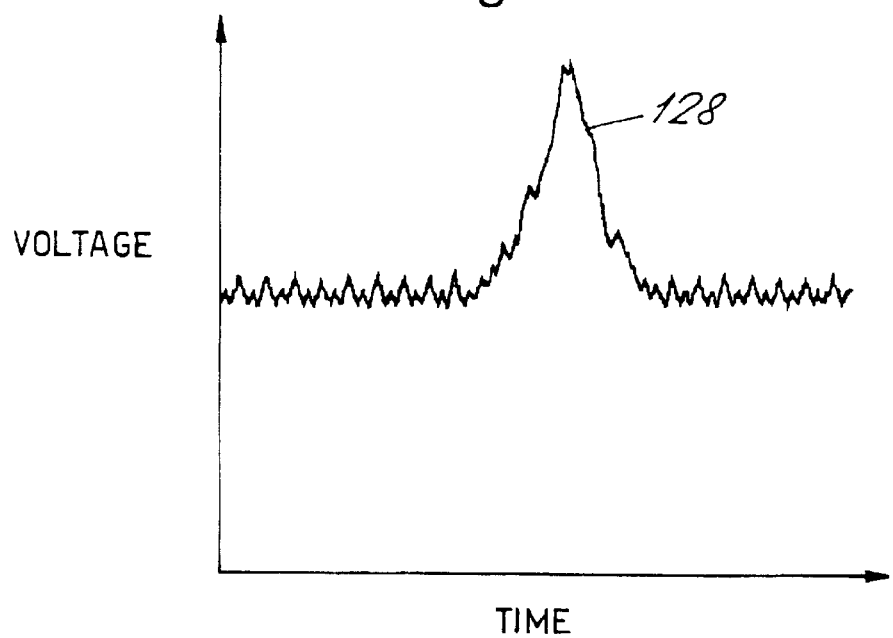
FIG. 10 is a typical plot of electrical voltage versus time across the aperture of the bead distribution apparatus.

The passage of beads through the aperture 54 in the pipette of the distribution head is detected by measuring changes in the electrical resistance across the aperture between electrodes 56 and 62. Preferably this is achieved by applying a current to the aperture by means of a constant current source 126, as shown in FIG. 8, and monitoring the voltage across the aperture. Alternating current is preferred in order to avoid the effects of polarization. The passage of a bead through the aperture results in an increase in the resistance across the aperture manifested by an increase in the voltage measured across the aperture. The voltage variation is depicted in FIG. 10, in which the voltage level remains essentially constant except when a bead passes through the aperture, at which time a voltage peak 128 appears. The peak is detected in the control unit and used to produce a signal to stop the operation of actuator 98 and pump 104.

As will be apparent from the description, the apparatus reliably selects individual beads from the mixture and deposits them in wells in the well plates.

Although the flow of liquid through aperture 54 is stopped almost immediately when the passage of a bead through the aperture is detected, occasionally, more than one bead will pass through the aperture into the pipette. The accidental passage of multiple beads through the aperture will be detected by the control system as a series of voltage peaks, and the control system responds by causing the distribution head to remain over the waste collector 25 while the beads are flushed out of the pipette. These beads can be reintroduced into the cup-shaped vessel 26 for later distribution. Waste liquid is delivered to a closed container 122, and a vacuum is drawn continuously on the waste collector 25, through container 122, by pump 120.

Figure 11:
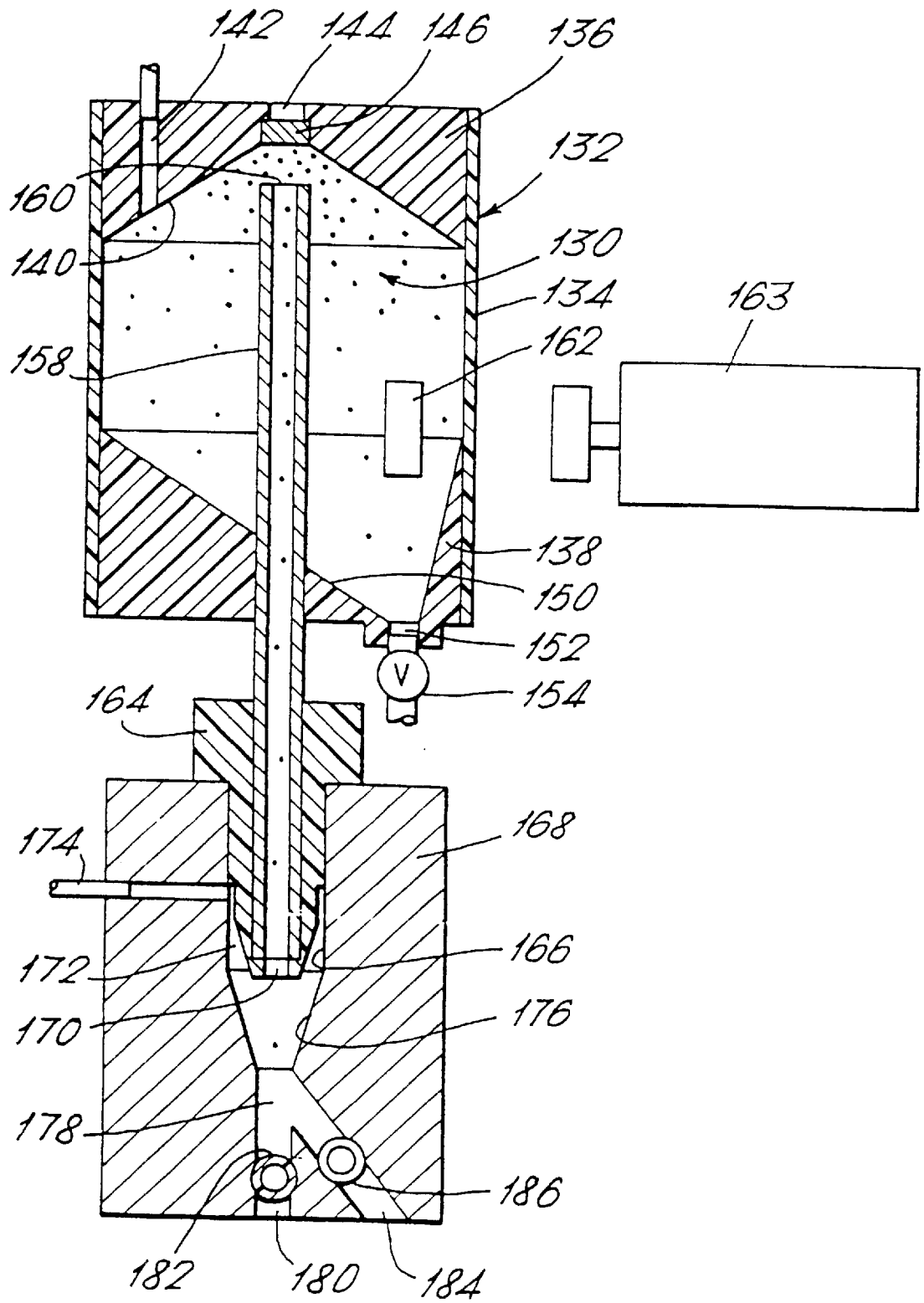
FIG. 11 is a schematic diagram showing a distribution head assembly in accordance with an alternative embodiment of the invention.

In the alternative embodiment shown in FIG. 11, a suspension of beads 130 is established in a vessel 132. The vessel comprises a cylinder 134 having a top closure 136 and a bottom closure 138. The top closure has a bottom face 140 in the form of a symmetrical cone. A fluid inlet is provided at 142, and an air outlet 144 at the peak of the cone has a filter 146. The bottom closure 138 has its top face 150 in the form of an asymmetric cone with an emptying port 152 provided with a valve 154.

A metal tube 158 extends upward through the bottom closure 138 to a location within the cone defined by bottom face 140 of the top closure. The tube is coaxial with that cone and has an opening 160 at its upper end for receiving beads along with liquid from the suspension 130. The beads are maintained in suspension by a magnetic flee 162 operated by an external magnetic stirrer 163.

The cone tends to concentrate beads at the location of the end opening 160 of tube 158, and beads enter the tube 158 along with liquid.

The lower part of tube 158 extends through the bottom closure 138 of the vessel 132, and into an insert 164 of PTFE or other similar material which is not electrically conductive. The insert fits into the upper end of a passage 166 in a metal block 168, and tube 158 extends into the insert to a location near, but spaced from the lower end of the insert. The lower end of the insert has an opening 170, having a diameter equal to the internal diameter of the tube 158 so that the tube and opening 170 form a continuous, smooth passage for the flow of liquid and beads.

The exterior of the lower end of insert 164 is narrower than the portion of passage 166 surrounding it, thereby providing an annular space 172 for the flow of liquid received through a passage 174. The liquid introduced through the passage 174 flows past the tip of insert 164, downwardly through a tapered part 176 of passage 166, and outwardly through an exit opening 178. The tip of the insert and the passage 166 are gradually tapered and shaped so that the flow past the tip of the insert is laminar.

The flow of liquid through passage 174 draws beads individually from the tip of insert 164 and delivers them into the upper part of passage 178, which serves as a collection chamber, from which they can be deposited in an array through opening 180. A solenoid-operated valve 182, located above opening 180, is movable in a direction perpendicular to the plane of the drawing to permit or block flow through opening 180. This valve is shown in its closed condition. A branch 184, communicating with passage 178, is provided with a similar solenoid-operated valve 186, which is shown in its opened condition. The valves 182 and 186 are provided with hollow internal passages through which liquid can be caused to flow for washing the passages 178 and 184.

In the apparatus of FIG. 11, the tube 158 serves as one of two electrodes, and block 168 serves as the other electrode. Passage of a bead through opening 170 effects a change in the electrical resistance measurable between tube 158 and block 168 in the same manner in which a bead passing though aperture 54 in FIG. 4 affects the resistance measured between electrodes 56 and 62. In the absence of an electrical signal produced by the passage of a bead through opening 170, valve 182 is closed and valve 186 is open, allowing liquid entering the block 168 through passage 174 to flow to waste through branch 184. The electrical signal produced in response to the passage of a bead controls the operation of valves 182 and 186 in such a way that valve 182 opens momentarily and valve 186 closes. The time delay between the detection signal and the operation of the valves is set in relation to velocity of movement of beads in the space below the tip of tube 158, so that valve 182 opens and valve 186 closes precisely at the time that the detected bead is in close proximity to the connection of the branch 184 to passage 178. The operation of the valves allows beads to be deposited individually into a suitable array, for example into wells in a microtitre plate.

In the apparatus of FIG. 11, the fluid introduced through passage 174 serves as a sheath fluid, and may be the same as the suspension fluid passing downwardly through tube 158 from vessel 132. The sheath fluid flows in the same direction in which the beads move through tube 158. Preferably, the suspension fluid and the sheath fluid flow through passage 178 in laminar flow, i.e. in substantially non-mixing layers respectively of the suspension fluid and the sheath fluid. Such laminar flow helps the beads to flow through passage 178 along a substantially straight path. the sheath fluid also helps to even out the flow of beads and assists in achieving suitable serial separation of beads. The sheath flow may be controlled to optimize the flow of beads through passage 178.

Various modifications can be made to the apparatus and process described. For example, by incorporating an electronic counter in the control unit, it is possible to count electrical peaks and disable the syringe actuator only after a predetermined number of peaks is counted. In this way, if desired, a preselected number of beads can be deposited in each well. The control system can be programmed to cause the beads in the pipette to be flushed into the waste collector if the number of beads passing through the aperture into the pipette exceeds the preselected number.

The pipette (with its aperture 54) can be readily removed for cleaning, or for replacement by another pipette having a different aperture. It is possible to eliminate the jewel 52 altogether, and thereby avoid the potential problems resulting from detachment of the jewel from the pipette. This can be done by forming the aperture directly in the wall of the pipette, provided that the wall thickness is sufficiently small.

In still another modification of the apparatus, openings are provided at the bottoms of the wells in the well plates, and filters are situated in the openings. A vacuum head is situated underneath the path of the distribution head and engageable with the undersides of the well plates. A vacuum is drawn continuously though the vacuum head, and is used to remove liquid form the wells. This keeps the wells from overflowing, and is an alternative to the previously described withdrawal of liquid from the upper end of the pipette at the same rate at which it enters the pipette through aperture 54.

In the embodiment of FIG. 11, various alternative valves and flow passage configurations can be used, and fluidic control can be utilized to divert the flow of liquid from one passage to another.

Still other modifications can be made to the apparatus and process without departing from the scope of the invention as defined in the following claims.

What is claimed is:

1. A process for distributing beads, from a mixture of beads of uniform size, into an array having multiple locations, so that a predetermined number of beads is deposited at each location in the array, comprising the steps of:

forming a suspension of the mixture of beads in a liquid;

causing at least a part of the liquid to flow, in a continuous stream, through a tubular passage alone with beads carried by the liquid, one after another, through the tube and outwardly from the tubular passage through an aperture;

causing liquid to flow from the aperture through a first path of a pair of paths by maintaining a valve in the other of said paths in a closed condition;

detecting the passage of a predetermined number of the beads through the aperture; and in response to the detection of the passage of said predetermined number of the beads through the aperture, causing the liquid to flow through the other of said paths by opening the valve in said other path while closing a valve in the first path, thereby depositing said predetermined number of beads at a predetermined location of the array.

2. The process according to claim 1 in which the liquid is electrically conductive, in which the tubular passage is defined in part by a conductive tube, and the aperture is defined by an insulating element, and in which the detecting step is carried out by monitoring the electrical resistance, across the aperture, between said conductive tube and an electrode external to said tubular passage.

3. The process according to claim 1 in which the liquid is electrically conductive, in which the tubular passage is defined in part by a conductive tube, and the aperture is defined by an insulating element, and in which the detecting step is carried out by establishing a constant electric current in the liquid through the aperture, between said conductive tube and an electrode external to said tubular passage, and monitoring the voltage across the aperture.

4. Apparatus for distributing beads, from a mixture of beads of uniform size, into an array having multiple locations, so that a predetermined number of beads is deposited at each location in the array, comprising:

means for containing a suspension comprising a mixture of beads suspended in a liquid;

means for collecting beads;

means providing a tubular passage leading from said containing means to the collecting means, said tubular passage having an outlet aperture;

means for causing liquid to flow through the tubular passage, and outwardly through the aperture, from the containing means to the collecting means;

means for detecting the passage of beads through the aperture;

means establishing a pair of paths branching from the aperture, each path having a valve, the valve in one of said paths being normally closed and the valve in the other of said paths being normally open; and means, responsive to the detecting means, for opening the valve in said one path and closing the valve in said other path, thereby depositing beads collected in the collecting means at predetermined locations in an array when the passage of a predetermined number of beads through the aperture is detected by the detecting means.

5. The apparatus according to claim 4, in which the tubular passage is defined in part by a conductive tube, and the aperture is defined by an insulating element, and having an electrode external to said tubular passage, and in which the means for detecting the passage of beads through the aperture comprises means for monitoring electrical resistance across the aperture, between said conductive tube and said electrode external to said tubular passage.

6. The apparatus according to claim 4, in which the tubular passage is defined in part by a conductive tube, and the aperture is defined by an insulating element, and having an electrode external to said tubular passage, and in which the means for detecting the passage of beads through the aperture comprises means for establishing a constant electric current in the liquid through the aperture, between said conductive tube and said electrode external to said tubular passage, and means for monitoring the voltage across the aperture.

\* \* \* \* \*